(12) United States Patent
Michel et al.

(10) Patent No.: US 7,214,213 B2
(45) Date of Patent: May 8, 2007

(54) DOSAGE DISPLAYING DEVICE

(75) Inventors: Reto Michel, Derendingen (CH);
Frank Schiffmann, Burgdorf (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 11/066,727

(22) Filed: Feb. 25, 2005

(65) Prior Publication Data

US 2005/0177114 A1    Aug. 11, 2005

Related U.S. Application Data

(63) Continuation of application No. PCT/CH2003/00533, filed on Aug. 7, 2003.

(30) Foreign Application Priority Data

Aug. 29, 2002    (DE) ................ 102 39 784

(51) Int. Cl.
*A61M 5/00* (2006.01)
(52) U.S. Cl. .................................. 604/207
(58) Field of Classification Search ................ 604/187, 604/189, 207–211, 246
See application file for complete search history.

(56) References Cited

U.S. PATENT DOCUMENTS

| 4,865,591 | A | * | 9/1989 | Sams .......................... 604/186 |
| 5,114,406 | A | * | 5/1992 | Gabriel et al. ............... 604/136 |
| 5,244,465 | A | * | 9/1993 | Michel ........................ 604/208 |
| 5,279,585 | A | * | 1/1994 | Balkwill ...................... 604/207 |
| 5,304,152 | A | * | 4/1994 | Sams .......................... 604/207 |
| 5,921,966 | A | * | 7/1999 | Bendek et al. .............. 604/207 |
| 5,947,934 | A | * | 9/1999 | Hansen et al. .............. 604/207 |
| 6,001,082 | A | * | 12/1999 | Dair et al. .................. 604/207 |
| 6,004,297 | A | * | 12/1999 | Steenfeldt-Jensen et al. .... 604/207 |
| 6,193,698 | B1 | | 2/2001 | Kirchhofer et al. |
| 6,221,046 | B1 | * | 4/2001 | Burroughs et al. ......... 604/153 |
| 6,235,004 | B1 | * | 5/2001 | Steenfeldt-Jensen et al. .... 604/207 |
| 6,364,860 | B1 | | 4/2002 | Steck et al. |
| 6,547,763 | B2 | * | 4/2003 | Steenfeldt-Jensen et al. .... 604/181 |
| 6,582,404 | B1 | * | 6/2003 | Klitgaard et al. ........... 604/181 |
| 6,613,023 | B2 | * | 9/2003 | Kirchhofer et al. ......... 604/208 |
| 6,692,472 | B2 | * | 2/2004 | Hansen et al. .............. 604/211 |

FOREIGN PATENT DOCUMENTS

WO    WO 02/064199 A1    8/2002

* cited by examiner

*Primary Examiner*—Nicholas Lucchesi
*Assistant Examiner*—Theodore J. Stigell
(74) *Attorney, Agent, or Firm*—Dorsey & Whitney LLP

(57) ABSTRACT

A device for displaying a dosage setting on an injection device includes a reading area in a casing of the injection device and a scale band arranged in the interior of the casing. The scale band is at least partially guided past the reading area by a guiding device, and can be set in accordance with a dosage setting of the injection device, and the dosage setting can be read from the reading area. A transport device, coupled to a dosage setting device of the injection device, is provided for transporting said scale band past the reading area.

17 Claims, 2 Drawing Sheets

DOSAGE DISPLAYING DEVICE

CROSS-REFERENCE TO RELATED APPLICATION(S)

This application is a continuation of International Application No. PCT/CH2003/00533, filed on Aug. 7, 2003, which claims priority to German Application No. DE 102 39 784.8, filed on Aug. 29, 2002, the contents of which are incorporated in their entirety by reference herein.

BACKGROUND

The present invention relates to devices and methods for delivering or administering substances, including injection, infusion or inhalation devices and methods for their manufacture and use. More particularly, it relates to devices, features, mechanisms or structures for displaying a dosage setting on an injection, infusion or inhalation device or the like.

In many infusion or injection devices, such as for instance infusion pumps or injection pens for administering insulin, it is possible to set different doses or dosages to be administered. In order to dose correctly when administering a medicine, it is necessary or at least helpful to be able to read the set dosage from the device. To this end, a scale can, for example, be attached to the outer surface of the casing of the device. The dosage to be administered may be set by, for example, a rotational mechanism with the aid of a dosing button. An indicator is simultaneously arranged on the dosing button and assigns the corresponding value on the scale of the casing to a particular dosage rotational position. Providing numerical wheels—for example, for the tens and units of the dosage to be administered—in the interior of the casing of an injection device is also known. The adjacent numerical wheels are rotated further in accordance with setting a dosage. A window is arranged in the wall of the casing, through which the display of the numerical wheels is visible. If the dosage is set with the aid of a threaded rod, it is also possible to attach a scale to said threaded rod. The value of a dosage set, which corresponds to a particular rotational position of the threaded rod, can again be read in a window of the casing of the injection device.

DE 102 29 122, belonging to the owner of the present application, shows, for example, an administering apparatus for an injectable product which comprises a dosage displaying sleeve in the interior of the apparatus, on which the dosage units are printed circumferentially in a spiral. This dosage displaying sleeve is moved relative to the casing by the dosing movement of a dosing and activating means, in order to display the selected product dosage. To this end, a cavity is provided in the part of the casing surrounding the dosage displaying sleeve, in which the dosage unit then appears. A reset cam protrudes from the dosage displaying sleeve, via which the dosage displaying sleeve presses a blocking member out of a blocking engagement with the dosing and activating means by which said means is prevented from moving counter to an activating direction. The dosage displaying sleeve only releases the blocking engagement when it is moved relative to the casing, into a zero-dosage position. This resets the size of the dosage and the display.

A device for dispensing a medicinal fluid in doses, comprising a resettable display means, is known from U.S. Pat. No. 6,364,860, belonging to the owner of the present application, the disclosure of which is incorporated herein by reference. The display means comprises a counting ring which is rotated out of a zero position by a setting movement of an activating means with respect to a casing. A shifting movement of the activating means is mechanically transferred, via a resetting means, into a rotational movement of the counting ring back into its zero position, whereby the counting ring is necessarily rotated continuously back.

U.S. Pat. No. 6,193,698, the disclosure of which is incorporated herein by reference, also belongs to the owner of the present application. It describes a device for administering an injectable product in doses, in which a first display sleeve fixed to the casing and a second display sleeve which can be rotated with the dosing button are provided in order to display the rotational position of the dosing button, i.e. the selected product dosage. One of the display sleeves surrounds the other. Dosage values are disposed on an annular scale of the inner display sleeve and can be read through a window in the outer display sleeve. A shifting block for the dosing button prevents the dosing button from shifting in an uncontrolled way. The dosing button can only be moved back if the display sleeves are in a zero position with respect to each other.

In these known dosage displays, the size of the numbers on the scale is often very small, or numerical values have to be replaced by bars, since sufficient space is not available. In most cases, a round shape of the casing and/or injection device is necessary for forming the mechanism of the dosage display. If the casing has an oval or polygonal shape, the numerical value cannot be arranged near enough to a window or indicator, such that a dosage setting is difficult to read. A dosage display using numerical wheels, or even a digital unit operated via a cam shaft arranged on the dosing rotational mechanism, also takes up a lot of space in the interior of the injection device.

SUMMARY

Objects of the present invention include providing a display device for devices for delivering or administering a substance, wherein the display shows the amount of the substance selected for delivery or administration. Another object of the present invention is to provide a display device for injection devices or the like, wherein the display device can be used with injection devices of various shapes, including variously shaped casings and various scale divisions, wherein it is easy to read, and wherein it is space-saving and inexpensive to manufacture.

These object are addressed by a device for displaying a dosage setting on an injection device in accordance with the present invention, wherein, in one embodiment, the device comprises a reading area on a casing of the injection device and a scale element arranged at least partially in the interior of the casing, wherein the scale element can be moved in accordance with setting a dose to be delivered by the injection device, a scale unit of the scale element corresponding to the dosage setting can be read from the reading area, wherein the scale element is provided by a scale strip which is at least partially guided past the reading area by a guiding device, and wherein a transport device for transporting the scale strip is provided adjacent to the reading area and is coupled to a dosage setting device of the injection device.

In one embodiment, the present invention comprises a device for displaying a dosage setting of an injection device comprising a reading area associated with the injection device, a scale band arranged in the injection device generally adjacent to the reading area, transport means operably coupled to dosage setting means for setting a dosage, the transport means for transporting said scale band past a portion of the reading area, and guiding means for at least partially guiding the scale band past the reading area. In some embodiments, the scale band can be set in accordance with a dosage setting of the injection device, and the dosage setting can be read from the reading area.

In one embodiment, the dosage displaying device of the present invention comprises a reading area in a casing of an injection device. The reading area can be provided by a window which is, for example, provided by a cavity in the casing or merely by a transparent area of the casing. If the casing is transparent, the reading area can be provided by an area highlighted in color, wherein the area can be outlined in color or filled in in color, as long as a scale can still be read through such a colored area. In some embodiments, a transparent window is provided in a casing which is opaque in its remaining area. The window may be arranged on a circumferential surface of the casing running in the longitudinal direction. The casing of the injection device can exhibit any shape, predetermined, for example, by the dosing or dispensing mechanism of the injection device. In some preferred embodiments, an oval shape of the casing is selected which is, for example, advantageous for handling the injection device or for the mechanism of the injection device. A scale strip is arranged behind the reading area in the interior of the casing and is preferably flexible. The two ends of the scale strip are also connected to each other, such that a closed scale band is formed. The ends of the scale strip can be connected to each other directly or via a connecting element. The scale strip and/or scale band is guided at least partially past the reading area by a guiding device in the interior of the casing. The scale band can thus be guided past, directly behind the reading area in the interior of the casing, such that the band almost abuts the casing and exhibits almost the same distance from the surface of the reading area, such as for instance a window surface, over the entire surface of the reading area. The surface is large enough that exactly one scale unit of the scale disposed on the scale strip and/or scale band can be read. When inscribing the scale band with the scale units, the units can be disposed either in the longitudinal direction or transversely with respect to the scale band.

It is, however, also possible to guide the scale band past, partially outside the casing, such that this part of the scale band forms the reading area. To this end, the scale band can be guided outwards through a slit in the casing and back into the casing through another slit. The distance between the slits is large enough that exactly one scale unit is visible on the area of the scale band on the outside. The slits form a part of the guiding device. A transport device moves the scale strip and/or scale band past the reading area, wherein the transport device is coupled to a dosage setting device of the injection device and is arranged in the interior of the casing. The coupling between the transport device and the dosage setting device may be formed to be releasable. If the correct dosage is set, the setting movement is terminated and this also stops the movement of the scale strip and/or scale band, such that the dosage can be read from the reading area.

The scale strip (which also might be referred to as the strip, band, scale or scale band) is, in some preferred embodiments, only flexible along a two-dimensional plane which runs perpendicular to a surface of the strip and along the length of the strip. The strip is formed so as to be rigid with respect to a movement out of this plane. It is, however, conceivable to flex the strip in a third dimension by rotating and/or twist the surface of the strip and therefore the two-dimensional plane. The scale strip can be formed so as to be continuous or can also be constructed from individual members which are connected into a kind of chain. In principle, however, the scale strip or band can be formed so as to be flexible in any direction.

A suitable scale strip or band can consist of metal which can, for example, be inscribed by a laser, since metal exhibits a suitable rigidity for inscribing and for guiding the band. It is, however, also possible to use plastic, wherein the scale strip or band can, for example, be directly attached while manufacturing the band. An elastic material can also be used, which enables the band to be easily tensed by being deflected. Care should then be taken that the band can still slide along the diverters if these cannot be rotated. A lens can be inserted into the window of the casing enlarge the apparent numerical value of the units on the scale band when observed from outside.

In accordance with a preferred embodiment of the present invention, the scale band is guided by the guiding device along the inner circumference of the casing, wherein the guiding device consists of a number of diverters for the band which can be provided by pins which protrude from the casing, parallel to the inner circumferential surface of the casing, into the casing. Preferably, the diverters protrude from a facing surface of the casing into the interior of the casing. The scale band is placed around these diverters and thus guided past the reading area in the desired way. The guiding device can also comprise a tensing or tensioning device which ensures that the band remains tensed and does not fall out of the guide.

It is also possible to guide the scale band not only along the inner circumferential surface of the casing, but also at least partially in the interior of the casing, in the form of a loop. To this end, it can be guided around the diverters in a serpentine manner. It is also possible to arrange the diverters in accordance with guiding the band in a desired way. Care should then merely be taken that the band is guided past at a small distance from a window in the casing, preferably in such a way that it exhibits the same distance from said surface over the entire window surface. In this way, there should be little or no distortion of the scale value when a lens is used in the window. If the band runs in the form of a loop, the length of the band can be varied. In this way, all the units of the scale can be written out and arranged in an easily legible size on the band, even if the scale has a broad range of units.

The transport device is coupled to a device for setting the dosage of the injection device. The volume of the dosage of a product to be injected may be, for example, varied in an injection device by limiting the movement of a dispensing piston by rotating a rotational button which cooperates with a threaded rod. In this way, the dosage space in the interior of the injection device is changed by rotating the rotational button which the user can access from outside. By coupling the transport device to such a dosage setting device, the scale band can be moved in proportion to the change in the dosage volume. The scale units are arranged on the band at a distance which corresponds to a change in the dosage space of one such unit.

The coupling between the transport device and the dosage setting device may be provided by a positive-lock connection such as complementary or co-operating teeth or the like, for example outer or inner teeth, texturing or toothing. To this end, the rotational button may comprise a toothed ring for setting the dosage in the interior of the casing. Another toothed ring is arranged on a rotatable transport pin which acts on the scale strip and/or scale band. The transport pin is preferably incorporated into the arrangement of diverters in accordance with a desired course of the scale band. The toothed ring of the rotational button and the toothed ring of the transport pin engage with each other, such that when the rotational button is rotated, the transport pin is also rotated. The distance of the units on the scale band should be adapted to the speed at which the scale band is guided past the reading area of the casing by rotating the rotational button and/or the transport pin.

In principle, it is also possible to provide the transport device with just one toothed ring on the rotational button, said toothed ring engaging directly with a transport area on the scale band corresponding to the teeth. To this end, the scale band must be guided by the diverters in such a way that said transport area can co-operate with the teeth of the rotational button.

In accordance with a preferred embodiment of the transport device, one or more suitable transfer structures, such as gears for gearing up or gearing down, are arranged between the teeth on the rotational button and the teeth on the transport pin. In this way, the transport speed of the scale band can, for example, be set to a desired value, such that the arrangement of the scale units on the scale band can be freely selected. When guiding the scale band, a double gearing up has proven to be advantageous. Slaving cams may also be arranged on the rotatable transport pin in the circumferential direction of the pin. The scale band is then provided with holes arranged at a distance which corresponds to the distance of the slaving cams on the transport pin. The scale band is placed around the transport pin in such a way that at least one of the slaving cams engages with at least one of the holes. When the transport pin is rotated by the transport device, the slaving cams engage sequentially with adjacent holes on the band and in this way transport the scale band past the window of the casing. In principle, however, the band could be transported solely by the friction of the band on a rotatable transport pin.

If a desired dosage is displayed by the dosage displaying device, i.e., if the required dosage of the injection device has been set, the dosage can be dispensed. To this end, it is possible for the rotational button for setting the dosage to simultaneously be a push button for dispensing the dosage. When dispensing the dosage, this rotational push button is pressed into the casing and in this way activates the dispensing mechanism. Once the dosage has been dispensed, the rotational push button returns to its initial position, in order to set the dosage for dispensing again by being rotated and to dispense this new dosage by being pressed. It is therefore necessary for the coupling between the transport device of the dosage displaying device and the dosage setting device of the injection device to be decoupled, for dispensing the dosage. When the rotational push button is pressed, the teeth between the toothed ring of the rotational button and another toothed ring of the transport device are therefore released. In this position, the dosage display cannot be rotated and the dosage setting also cannot be changed while the dosage is dispensed. When the rotational push button returns to its initial position, the toothed ring of the dosage setting device and the toothed ring of the transport device engage with each other again. To this end, the toothed rings can be chamfered at their edges in order to enable easier engaging. It is then possible to set another dosage and for this to be displayed by the dosage displaying device. Alternatively, the dosage displaying device in accordance with the invention can also be combined with the resetting mechanisms known from the prior art outlined at the beginning. It is also conceivable to employ a resetting mechanism such as is known from WO 02/24260 in conjunction with the dosage displaying device. In WO 02/24260, a resetting spring which is secured when tensed is coupled to the activating device by a release, such that a resetting movement of the activating device towards an initial dosage position is generated.

If the dispensing mechanism is independent of the dosage setting mechanism, it is not necessary for the transport device to be decoupled from the dosage setting device. Therefore, instead of teeth on the rotational button, the transport device could also, for example, comprise a rubber band which is placed around the rotatable transport pin and the rotational button. Due to the friction of the rubber band on the rotational button and the transport pin, the rotation is therefore transferred and the scale band is transported.

Due to the variable guiding of the scale strip or band in the interior of the casing, a dosage display device in accordance with the present invention can be employed for virtually any shape of the casing. In each case, the dosage display can easily be read from the reading area on the casing, since by suitably arranging the diverters, the band can in each case be arranged directly behind a window or suitably guided past on the outside. The dosage displaying device is suitable for many various scale means and scale lengths, since the length of the band can be varied by various possible courses of the scale band in the interior of the casing. The dosage displaying device can be arranged in a space-saving way on the inner circumference of the casing, such that the middle space of the casing remains free for other devices. The dosage displaying device is also inexpensive to manufacture, since it is composed of few, basic components. The device of the present invention for displaying a dosage setting has been illustrated by way of the example of an injection device. It is, however, equally possible to employ the dosage displaying device in an infusion device, an inhalation device or other device.

Other objects, features and advantages of the present invention may be understood with reference to the accompanying drawings and description, and the appended claims.

DETAILED DESCRIPTION

Figure 1:
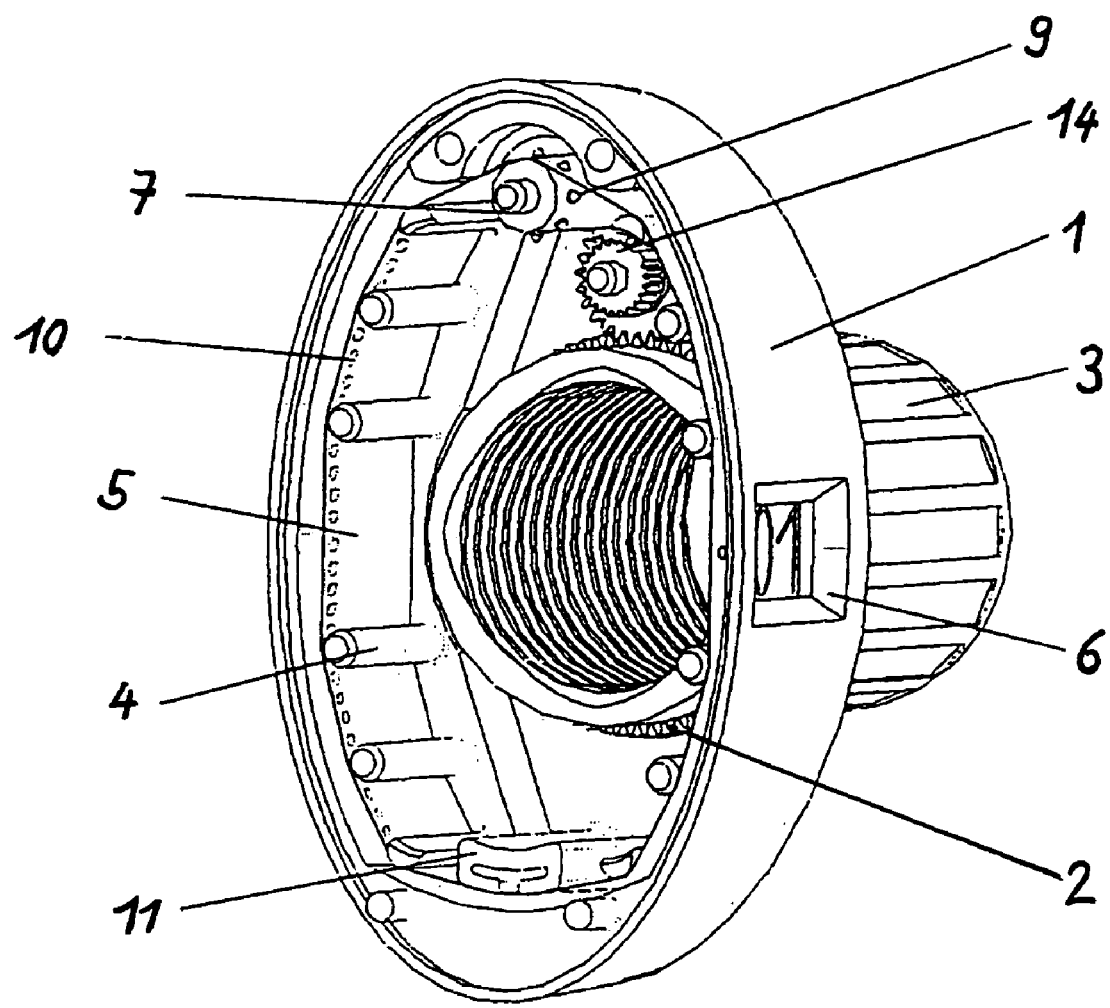
FIG. 1 is a perspective view of a section through an injection device comprising the dosage displaying device in accordance with the invention.

FIG. 1 shows a part of a casing 1 of an injection device in whose interior a device in accordance with the present invention for displaying a dosage setting is shown. A rotational button 3 protrudes out of the casing 1 at one end and comprises a toothed ring 2 in the interior of the casing 1. The rotational button 3 serves to set the dosage of the injection device and is simultaneously a part of a transport device of the dosage displaying device. Diverters 4 in the form of pins protrude from the facing surface of the casing 1 into the interior of the casing 1. The pins can be fixed or rotatable. A closed scale band 5 is arranged around the diverters 4 and in the example shown is guided along the inner circumferential surface of the casing 1 by the diverters 4. A unit value of the scale division disposed on the band 5 can be seen through a window 6 in the circumference of the casing 1. To this end, the scale on the scale band 5 is attached to the surface pointing towards the inner wall of the casing 1.

A rotatable transport pin 7 protrudes inwards into the casing 1 from the facing surface of the casing, and the scale band 5 is guided around the transport pin 7. The transport pin 7 is provided with a toothed ring 8 at a lower end bordering the facing surface of the casing 1 and with slaving cams 9 at an upper end away from the facing surface. Holes 10 are provided in the scale band 5, with which the slaving cams 9 of the transport pin 7 engage. A tensing means 11 is arranged opposite the transport pin 7, in order to tense the band 5 running around the diverters 4. Any tensing device can be used to this end, such as for instance an elastically biased element. The tensing element shown in FIG. 1 is, for example, formed as a pad with two fins arranged on the rim of the pad and protrudes inwards from the facing surface of the casing 1. The fins point substantially along a side of the pad from the rim to the middle of the pad, but are slightly flared outwards, such that they are biased when a force acts on the lateral surface of the pad formed by the fins. The scale band 5 is guided along this lateral surface, wherein it exerts a force on the fins of the tensing means 11 and is tensed by the restoring force of the element. The diverters 4, the rotatable transport pin 7 and the tensing means 11 form the guiding device for the scale band of the dosage displaying device as set forth in the present invention.

Figure 2:
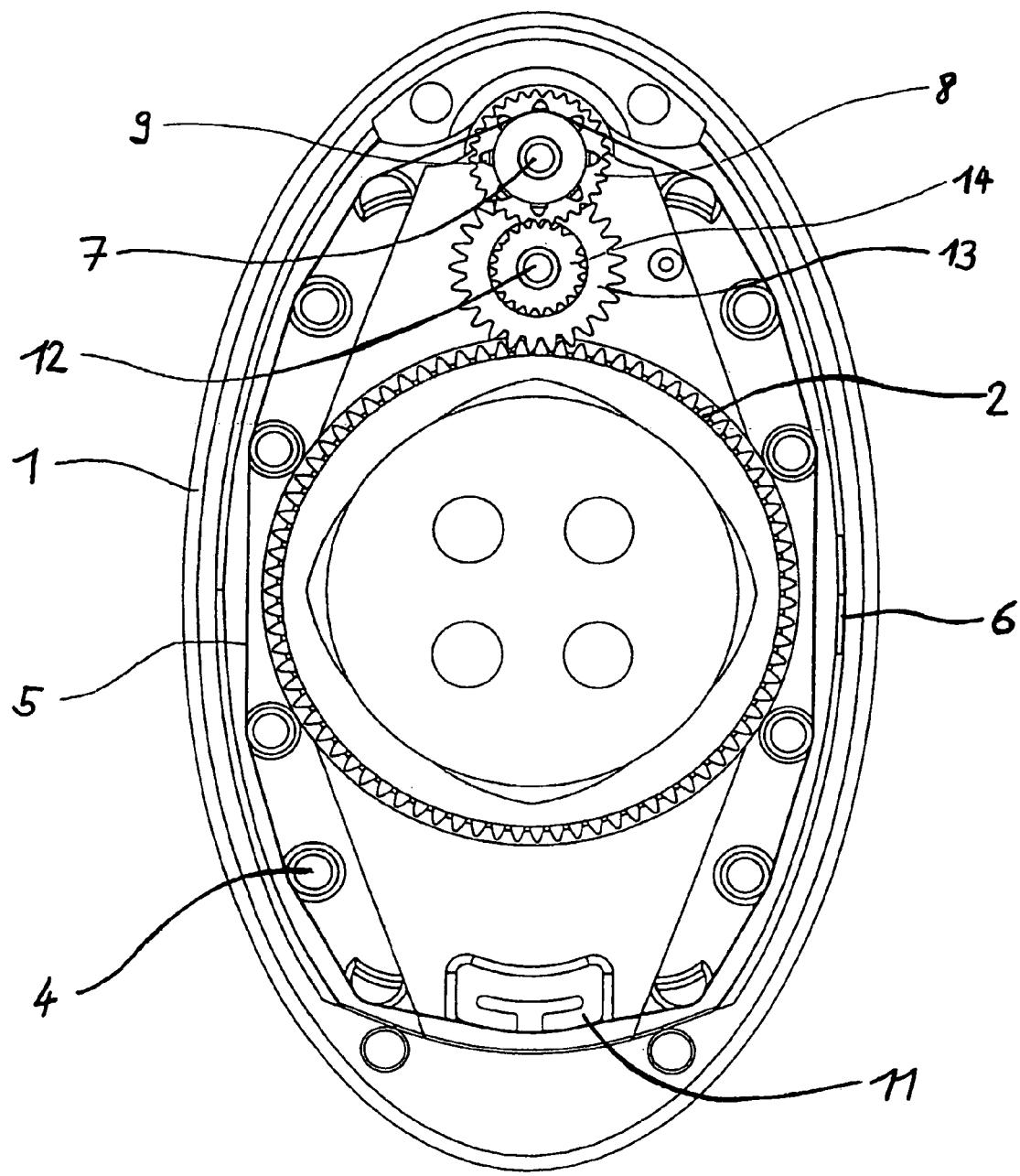
FIG. 2 is a cross-section through an injection device comprising the dosage displaying device in accordance with the present invention.

In FIG. 2, a cross-section through the casing 1 of the injection device shows the entire course of the scale band 5. The scale band 5 runs around the diverters 4, the tensing means 11 and the rotatable transport pin 7, wherein the slaving cams 9 of the transport pin 7 protrude through the holes 10 of the scale band 5. A pin 12 is arranged between the rotational button 3 and the transport pin 7 and comprises a first toothed ring 13 and a second toothed ring 14, wherein the first toothed ring 13 engages with the toothed ring 2 of the rotational button 3 and the second toothed ring 14 engages with the toothed ring 8 of the transport pin 7. The toothed rings 13 and 14 transfer the rotational movement of the rotational button 3 onto the transport pin 7, wherein a desired transfer ratio is achieved by suitably selecting the size of the toothed rings. By selecting the transfer, the rotational speed of the transport pin 7 and thus the speed of the scale band can be set. The scale band 5 is guided along, near to the inner circumference of the casing 1, by the diverters 4. It is guided past at a small distance from the window 6, wherein the distance between the window 6 and the scale band 5 remains approximately the same over the entire surface of the window. A lens can be inserted in the window 6, for example in the form of a plastic lens (not shown), in order to further facilitate reading the unit.

When administering a product, a required dosage is set on the injection device by rotating the rotational button 3. Via the toothed ring 2, rotating the rotational button 3 also moves the first toothed ring 13 on the pin 12, thus transferring the rotation onto the transport pin 7 via the second toothed ring 14 on the pin 12 and the toothed ring 8. Rotating the transport pin 7 transports the scale band 5 in accordance with setting a dosage, such that once the dosage setting rotation is complete, the corresponding dosage unit can be read through the window 6. In order to administer the product, the rotational button 3 is pressed into the interior of the casing, wherein the mesh or connection between the toothed ring 2 and the toothed ring 13 is decoupled. After administering, the rotational button 3 returns to its non-pressed position, wherein the two toothed rings 2 and 13 engage with each other again. A new dosage can then be set, with the scale being correspondingly set.

In the foregoing, embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising a dosage displaying device for displaying a dosage setting of an injectable product on the injection device, the dosage displaying device comprising a reading area on a casing of the injection device and a scale element arranged at least partially in the interior of the casing, wherein the scale element can be moved in accordance with setting a dosage, and a scale unit of the scale element corresponding to the dosage setting can be read from the reading area, wherein:

the scale element is provided by a scale strip which is at least partially guided past the reading area by a guiding device, the guiding device comprising diverters protruding from a facing surface of said casing into an interior of said casing, the diverters guiding the scale strip along the inside of said casing; and a transport device for transporting the scale strip is provided adjacent to the reading area and is coupled to a dosage setting device of the injection device.

2. The injection device as set forth in claim 1, wherein the scale strip is flexible.

3. The injection device as set forth in claim 1, wherein the scale strip is guided at least partially along the inner circumferential surface of the casing.

4. The injection device as set forth in claim 1, wherein the scale strip is guided at least partially through the interior of the casing in the form of a loop.

5. The injection device as set forth in claim 1, wherein the scale strip is a closed band.

6. The injection device as set forth in claim 1, wherein the scale strip is made of metal or plastic.

7. The injection device as set forth in claim 1, wherein the transport device is detachably coupled to the dosage setting device of the injection device.

8. The injection device as set forth in claim 1, wherein the transport device comprises a toothed ring on a rotational button for setting the dosage and a toothed ring on a rotatable transport pin which acts on the scale strip.

9. The injection device as set forth in claim 8, wherein the transport device further comprises at least one diverting gear.

10. The injection device as set forth in claim 9, wherein a transfer is provided between the toothed rings.

11. The injection device as set forth in claim 10, further comprising slaving cams arranged on the circumference of the rotatable transport pin and holes are arranged along the scale strip, wherein at least one of the slaving cams engages with at least one of the holes.

12. The injection device as set forth in claim 1, wherein a lens is provided in the reading area of the casing.

13. The injection device according to claim 1, wherein the diverters comprise fixed pins in relation to the scale strip.

14. The injection device according to claim 1, wherein the diverters comprise rotatable pins in relation to the scale strip.

15. An injection device comprising a dosage displaying device for displaying a dosage setting of an injectable product on an injection device, the dosage displaying comprising a reading area on a casing of the injection device and a scale element arranged at least partially in the interior of the casing, wherein the scale element can be moved in accordance with setting a dosage, and a scale unit of the scale element corresponding to the dosage setting can be read from the reading area, wherein:

the scale element is provided by a scale strip which is at least partially guided past the reading area by a guiding device, the guiding device comprising a tensioning device for tensing the scale strip; and a transport device for transporting the scale strip is provided adjacent to the reading area and is coupled to a dosage setting device of the injection device.

16. An injection device comprising a dosage displaying device for displaying a dosage setting of an injectable product on an injection device, the dosage displaying device comprising:

a reading area associated with a casing of the injection device;

a flexible scale strip arranged at least partially in the interior of the casing, wherein the flexible scale strip can be moved in accordance with setting a dosage, and a scale unit of the scale strip corresponding to the dosage setting can be read from the reading area;

a transport device coupled to a dosage setting device for transporting the flexible scale strip adjacent to the reading area in response to movement of the dosage setting device; and a guiding device comprising a plurality of guiding pins extending from the casing for guiding movement of the flexible scale strip within said casing.

17. The injection device according to claim 16, wherein the guiding device further comprises a tensioning device for tensing the flexible scale strip against said guiding device guiding pins and said transport device.

* * * * *